(12) United States Patent
Sajja et al.

(10) Patent No.: US 7,977,478 B2
(45) Date of Patent: Jul. 12, 2011

(54) POLYMORPHIC FORMS OF VARDENAFIL

(75) Inventors: Eswaraiah Sajja, Hyderabad (IN);
Ravindar Reddy Koppera, Hyderabad (IN); Satyanarayana Revu, Hyderabad (IN); Venkata Reddy Vajrala, Hyderabad (IN); Vijayapal Reddy Kanumathi, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 740 days.

(21) Appl. No.: 11/535,704

(22) Filed: Sep. 27, 2006

(65) Prior Publication Data
US 2007/0197535 A1 Aug. 23, 2007

Related U.S. Application Data

(60) Provisional application No. 60/786,585, filed on Mar. 28, 2006, provisional application No. 60/788,253, filed on Mar. 31, 2006, provisional application No. 60/806,816, filed on Jul. 10, 2006.

(30) Foreign Application Priority Data

Mar. 13, 2006 (IN) .............................. 447/CHE/2006

(51) Int. Cl.
C07D 487/04 (2006.01)
A61K 31/53 (2006.01)
A61P 15/10 (2006.01)

(52) U.S. Cl. ....................................... 544/184; 514/243

(58) Field of Classification Search .................. 544/184; 514/243
See application file for complete search history.

(56) References Cited

U.S. PATENT DOCUMENTS

| 6,362,178 B1 * | 3/2002 | Niewohner et al. ............ 514/218 |
| 2005/0203298 A1 * | 9/2005 | Nowakowski et al. ......... 544/60 |
| 2006/0111354 A1 * | 5/2006 | Serno et al. ................... 514/243 |

FOREIGN PATENT DOCUMENTS

WO WO 2004006894 A1 * 1/2004

OTHER PUBLICATIONS

Infantes, et al., Organic crystal hydrates: what are the important factors for formation, CrystEngComm, 2007, 9, pp. 65-71.
Vippagunta, et al., Crystalline solids, Advanced Drug Delivery Reviews, 2001, 48, pp. 3-26.
Grant, David J.W., Annual Report of the University of Minnesota Supercomputing Institute, 1999, p. 4 [retrieved from the internet on Feb. 12, 2003].

* cited by examiner

*Primary Examiner* — Venkataraman Balasubramanian
(74) *Attorney, Agent, or Firm* — Robert A. Franks; Balaram Gupta; Thomas C. McKenzie

(57) ABSTRACT

Crystalline polymorphic forms of vardenafil and vardenafil hydrochloride, and processes for preparing them.

6 Claims, 16 Drawing Sheets

POLYMORPHIC FORMS OF VARDENAFIL

INTRODUCTION TO THE INVENTION

The present invention relates to polymorphic forms of vardenafil and its pharmaceutically acceptable salts.

Chemically vardenafil hydrochloride is piperazine, 1-[[3-(1,4-dihydro-5-methyl-4-oxo-7-propylimidazo[5,1-f][1,2,4]triazin-2-yl)-4-ethoxyphenyl]sulfonyl]-4-ethyl-, mono -hydrochloride and can be structurally represented by Formula I.

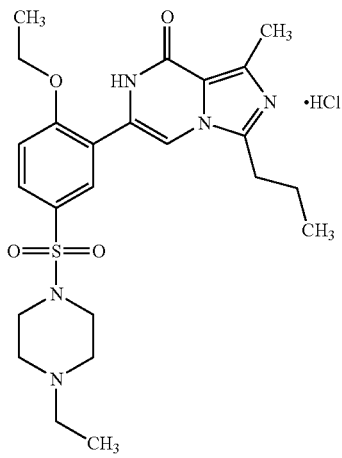

Formula I

The monohydrochloride salt of vardenafil is a selective inhibitor of cyclic guaosine monophosphate (cGMP)-specific phosphodiesterase type 5 (PDE5). It is commercially available in products sold under the brand name LEVITRA formulated as 2.5 mg, 5 mg, 10 mg, 20 mg film-coated tablets.

U.S. Pat. No. 6,362,178 B1 discloses vardenafil, its related compounds and processes for their preparation. The patent describes a process in which vardenafil is obtained by recrystallization in ether in Example 19. Vardenafil produced as per Example 19 is hereinafter referred as "crystalline Form I" of vardenafil. The patent also describes processes for the preparation of its monohydrochloride and dihydrochloride salts, which are formed in a combination of ether and dichloromethane. The patent also describes a process for the preparation of vardenafil monohydrochloride trihydrate.

U.S. Patent Application Publication No. 2005/0203298 also describes a process for the preparation of vardenafil, and its monohydrochloride trihydrate.

Chemical synthesis of vardenafil has mostly been directed to the preparation of the trihydrate of monohydrochloride of vardenafil.

A considerable amount of work needs to be done on the polymorphic characterization of vardenafil to identify other forms that can be generated.

Regulatory authorities throughout the world require that all possible crystalline forms of the same active compound be synthesized and characterized as completely as possible. It is also required that the commercial product should not contain traces of any of the other forms or, if present, the percentages of each of the forms be well characterized to avoid changes in the dissolution and bioavailability characteristics of drug substance during storage.

There is thus a continuing need to prepare new polymorphic forms of pharmacologically active compounds of commercial interest such as vardenafil, which provide the pharmaceutical formulation scientist with a broader spectrum of polymorphic forms of an active ingredient to choose from, based on their differing physiochemical properties.

It is also important that the processes for the preparation of the polymorphic forms be robust and reproducible, so that the processes are easily scaled up in the plant.

The present invention provides polymorphic forms of vardenafil and processes for their preparation, which are easily scaleable and commercially viable.

SUMMARY OF THE INVENTION

Certain aspects of the present invention relates to polymorphic forms of vardenafil and its pharmaceutically acceptable salts.

One aspect of the invention provides crystalline Form II of vardenafil characterized by its X-ray powder diffraction ("XRPD") pattern, infrared absorption ("IR") spectrum, differential scanning calorimetry ("DSC") curve, and thermogravimetric analysis ("TGA") curve.

Another aspect of the invention provides a process for the preparation of the crystalline Form II of vardenafil free base comprising the steps of:

a) providing a solution of vardenafil in a suitable solvent;
b) crystallizing the solid from the solution; and
c) recovering crystalline Form II of vardenafil free base.

Yet another aspect of the invention provides the amorphous form of vardenafil monohydrochloride characterized by its XRPD, IR, DSC, and TGA.

Yet another aspect of the invention provides a process for the preparation of amorphous form of vardenafil monohydrochloride comprising the steps of:

a) providing a solution of vardenafil in a suitable solvent;
b) removing the solvent; and
c) optionally, drying the solid.

Still another aspect of the invention provides crystalline hydrates of vardenafil dihydrochloride characterized by their XRPD patterns, DSC, and TGA.

Still another aspect of the invention provides processes for the preparation of crystalline hydrates of vardenafil hydrochloride comprising the steps of:

a) providing a solution of vardenafil in a suitable solvent;
b) adding 2 moles of hydrochloric acid;
c) crystallizing the solid from the solution; and
d) drying the solid.

A still further aspect of the invention provides a pharmaceutical composition comprising vardenafil or its pharmaceutically acceptable salts prepared in accordance with this invention along with one or more pharmaceutically acceptable carriers, excipients or diluents.

DETAILED DESCRIPTION OF THE INVENTION

One aspect of the invention provides crystalline Form II of vardenafil characterized by its X-ray powder diffraction pattern (XRPD), infrared absorption spectrum (IR), differential scanning calorimetry (DSC) curve, and thermogravimetric analysis (TGA) curve.

Crystalline Form II of vardenafil is characterized by its XRPD pattern, which differs from crystalline Form I of vardenafil described in the prior art. The XRPD data reported herein were obtained using Cu Kα-1 radiation, having the wavelength 1.541 A, and was measured on a Bruker Axe, D8 Advance Powder X-ray Diffractometer.

Figure 1:
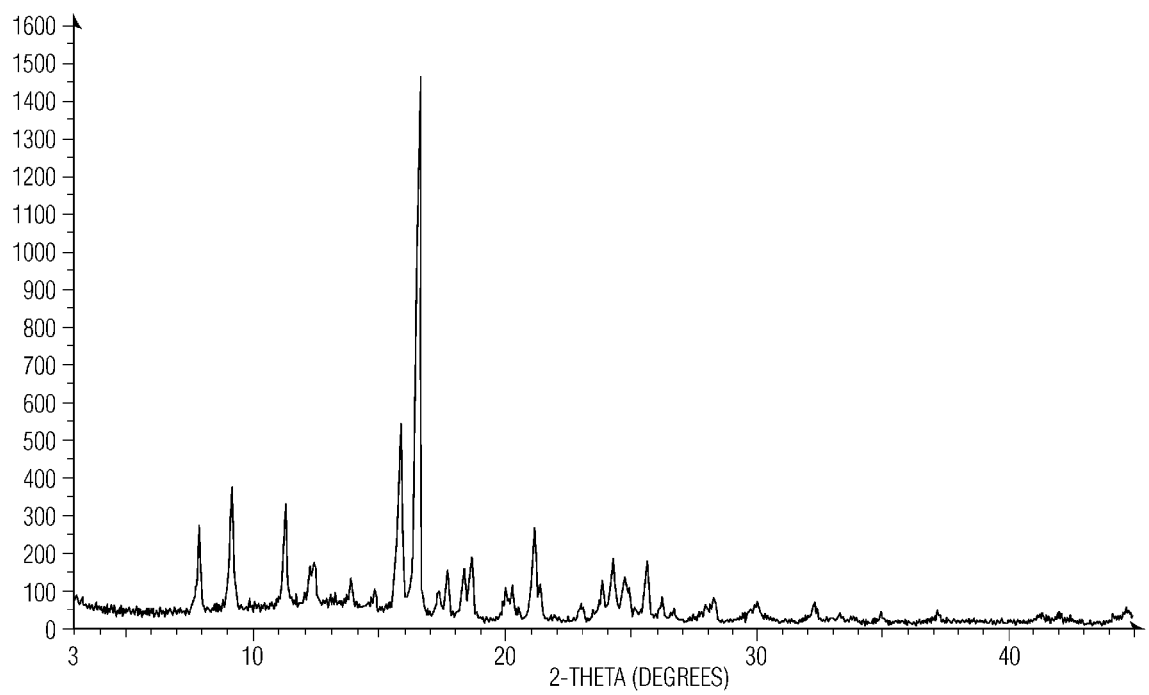
FIG. 1 is an XRPD pattern of the crystalline Form II of vardenafil prepared in Example 1.

The crystalline Form II of vardenafil is characterized by its XRPD pattern substantially in accordance with the pattern of FIG. 1. The crystalline Form II of vardenafil is also characterized by an XRPD pattern having significant peaks at about 16.4, 11.2, 15.8, 13.8, 7.8, 9.1, 17.3, 17.6, 18.3, 23.7, 24.2, 24.3, 24.6, 25.5, and 12.3, ±0.2 degrees 2θ. It is also characterized by additional XRPD peaks at about 18.5, 19.9, 20.2, 21.1, 21.3, and 22.9, ±0.2 degrees 2θ.

The comparison of 2θ values (in degrees) and % intensity between crystalline Form I and Form II of vardenafil free base is given in the following table.

| Form I | | Form II | |
|---|---|---|---|
| Angle 2θ | Intensity % | Angle 2θ | Intensity % |
| 4.7 | 100 | 16.4 | 100 |
| 9.6 | 41.3 | 15.8 | 42.8 |
| 24.5 | 14 | 11.2 | 31.6 |
| 17.0 | 11.1 | 9.1 | 25.3 |
| 16.0 | 10.6 | 18.5 | 24.1 |
| 20.0 | 10.1 | 21.1 | 22.7 |
| 12.3 | 9.5 | 17.6 | 20.8 |
| 23.1 | 6.4 | 7.8 | 15.6 |
| 21.5 | 6.2 | 24.3 | 13 |
| 15.2 | 5.6 | 24.6 | 13 |
| 27.2 | 5.6 | 12.3 | 12.4 |

The infrared spectra of the crystalline Form II of vardenafil has been recorded on Perkin Elmer System 200 FT-IR spectrophotometers, between 400 cm$^{-1}$ and 4000 cm$^{-1}$, with a resolution of 4 cm$^{-1}$, in a potassium bromide pellet, the test compound being at the concentration of 0.5% by mass.

Figure 2:
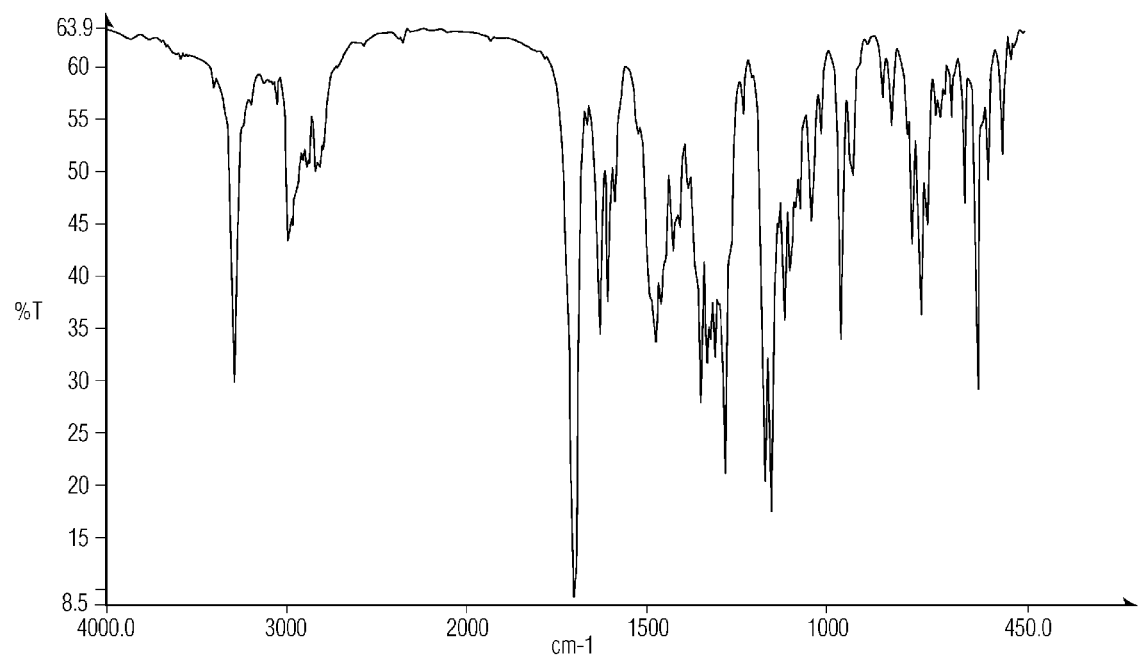
FIG. 2 is an IR spectrum of the crystalline Form II of vardenafil prepared in Example 1.

The crystalline Form II of vardenafil is characterized by an infrared absorption spectrum comprising peaks at about 583, 737, 956, 1114, 1169, 1151, 1345, 1625, 1701, and 3274, ±5 cm$^{-1}$. The crystalline Form II of vardenafil is also characterized by an infrared absorption spectrum substantially in accordance with the spectrum of FIG. 2.

Figure 3:
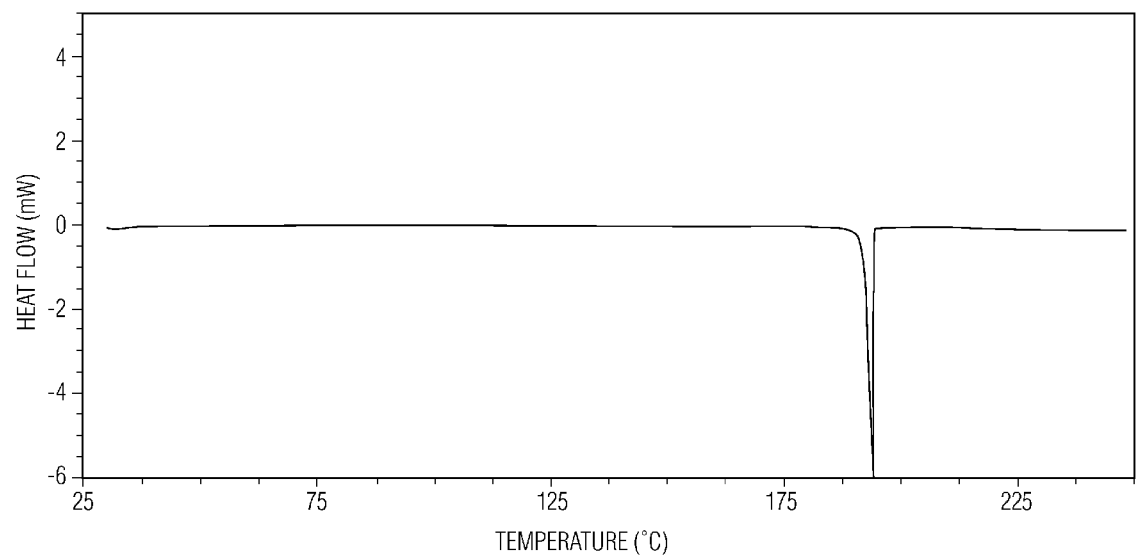
FIG. 3 is a DSC curve of the crystalline Form II of vardenafil prepared in Example 1.

The crystalline Form II of vardenafil is still further characterized by a differential scanning calorimetry curve substantially in accordance with the curve of FIG. 3. The Crystalline Form II of vardenafil is also characterized by a DSC curve having an endotherm at about 193° C.

Figure 4:
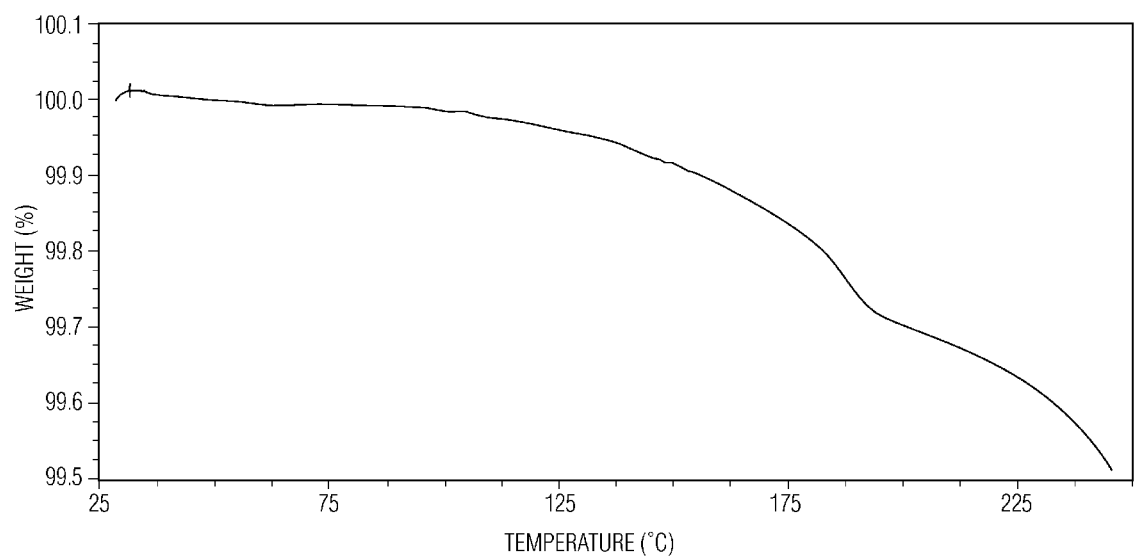
FIG. 4 is a TGA curve of the crystalline Form II of vardenafil prepared in Example 1.

The Crystalline Form II of vardenafil is yet further characterized by a thermogravimetric analysis curve substantially in accordance with the DTA curve of FIG. 4.

Another aspect of the invention provides a process for the preparation of the crystalline Form II of vardenafil free base.

In an embodiment, the process for the preparation of crystalline Form II of vardenafil free base comprises;

a) providing a solution of vardenafil in a suitable solvent;

b) crystallizing the solid from the solution; and c) recovering crystalline Form II of vardenafil free base.

Step a) involves providing a solution of vardenafil.

Vardenafil for the purpose of dissolution can be obtained by any of the process described in the prior art.

The solution of vardenafil may be obtained by dissolving vardenafil in a suitable solvent, or such a solution may be obtained directly from a reaction in which vardenafil is formed.

When the solution is prepared by dissolving vardenafil in a suitable solvent, any form of vardenafil such as the crystalline or amorphous form, including any salts, solvates and hydrates may be utilized for preparing the solution.

Suitable solvents which can be used for dissolving vardenafil include, but are not limited to: alcohols such as methanol, ethanol, isopropyl alcohol, n-propanol, and the like; ketones such as acetone, ethyl methyl ketone, methyl isobutyl ketone and the like; nitriles such as acetonitrile, propionitrile and the like; or mixtures thereof or their combinations with water in various proportions.

The dissolution temperatures can range from about 20 to 120° C. depending on the solvent used for dissolution. Any other temperature is also acceptable as long as a clear solution of vardenafil is provided.

The quantity of solvent used for dissolution depends on the solvent and the dissolution temperature adopted. The concentration of vardenafil in the solution may generally range from about 0.1 to about 10 g/ml in the solvent.

Optionally, the solution obtained above can be filtered to remove any undissolved particles.

The undissolved particles can be removed suitably by filtration, centrifugation, decantation, and other techniques. The solution can be filtered by passing through paper, glass fiber, or other membrane material, or a bed of a clarifying agent such as celite. Depending upon the equipment used and the concentration and temperature of the solution, the filtration apparatus may need to be preheated to avoid premature crystallization.

Step b) involves crystallizing the solid from the solution.

For crystallization to occur, the solution obtained in step a) may be maintained further at temperatures lower than the solution formation or concentration temperatures, such as for example below about 10° C. to about 25° C., for a period of time as required for a more complete isolation of the product. The exact cooling temperature and time required for complete isolation can be readily determined by a person skilled in the art and will also depend on parameters such as concentration and temperature of the solution or slurry.

Optionally isolation may be enhanced by methods such as cooling, partial removal of the solvent from the mixture, by adding an anti-solvent to the reaction mixture or a combination thereof.

Optionally, small amounts of seeding crystals of vardenafil crystalline Form II may be added to the reaction mixture. Suitably, small amounts are about 1 to 20 weight %, more preferably about 5 weight %. Seeding crystals may be added before or, where appropriate, after the step initiating the precipitation.

Step c) involves recovering crystalline Form II of vardenafil free base.

The crystalline Form II of vardenafil can be recovered from the reaction mass using techniques such as filtration by gravity, or by suction, centrifugation, and the like. The crystals so isolated can carry a small proportion of occluded mother liquor. If desired, the crystals can be washed on the filter with a solvent.

Optionally, the wet solid obtained can be dried. Drying can be carried out at reduced pressures, such as below 200 mm Hg or below 50 mm Hg, at temperatures of about 50° C. to about 80° C. The drying can be carried out for any desired or required time periods, such as for example about 1 to 20 hours being suitable for preparing some products.

Another aspect of the invention provides amorphous vardenafil monohydrochloride characterized by its X-ray powder diffraction (XRPD) pattern, differential scanning calorimetry (DSC) curve, and thermogravimetric analysis (TGA) curve.

Figure 5:
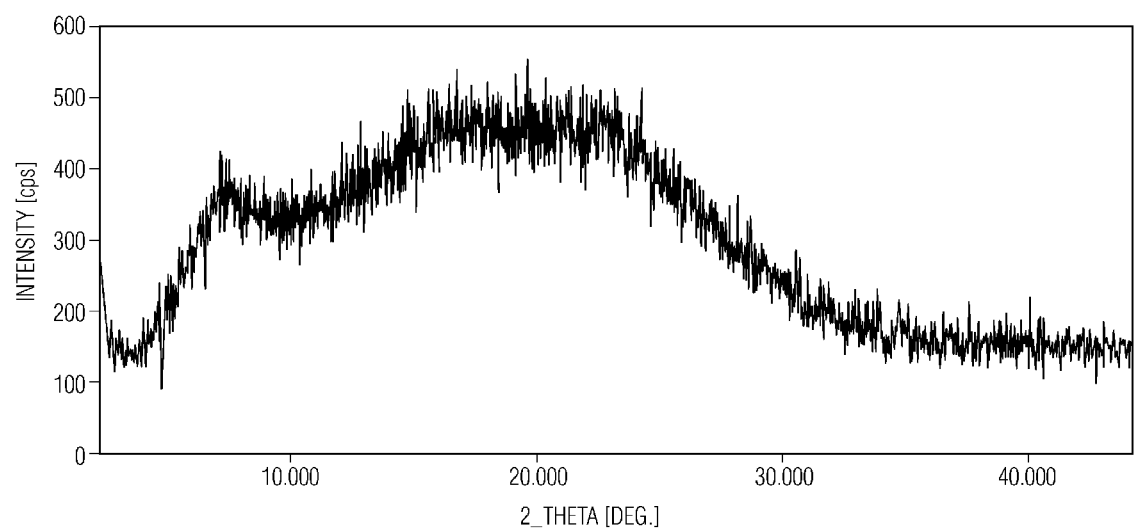
FIG. 5 is an XRPD pattern of the amorphous form of vardenafil monohydrochloride prepared in Example 2.

Amorphous vardenafil monohydrochloride is characterized by its XRPD pattern showing a plain halo with no peaks, which is characteristic of an amorphous solid, substantially in accordance with FIG. 5.

Figure 6:
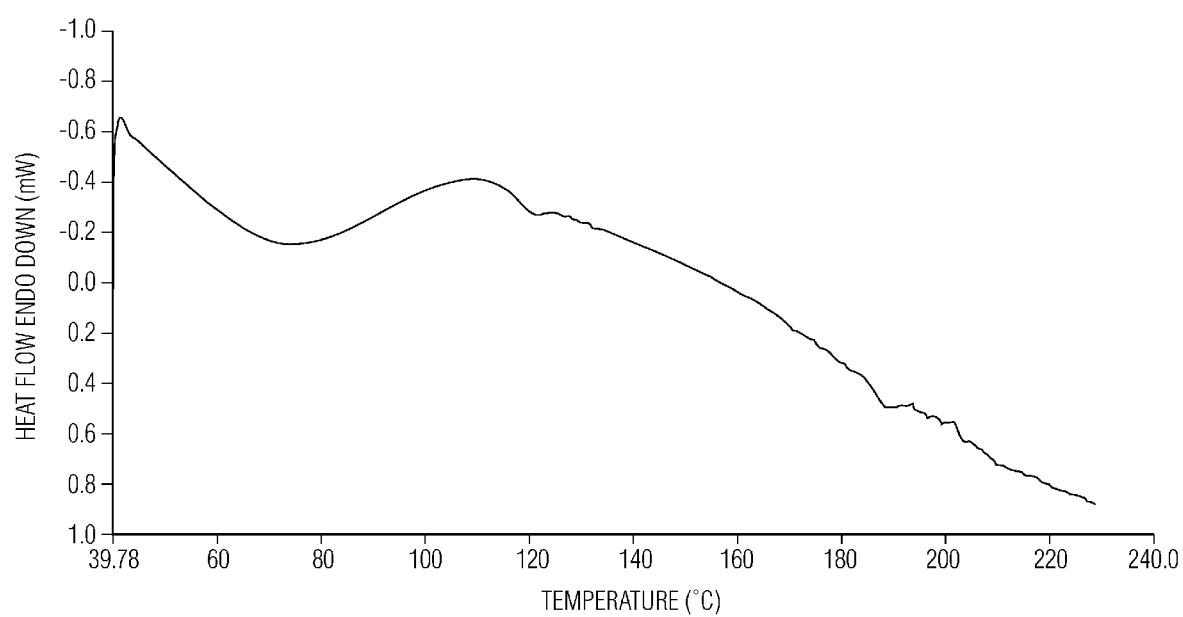
FIG. 6 is a DSC curve of the amorphous form of vardenafil monohydrochloride prepared in Example 2.

Amorphous vardenafil monohydrochloride is further characterized by a differential scanning calorimetry curve substantially in accordance with the curve of FIG. 6. Amorphous vardenafil monohydrochloride is also characterized by a DSC curve having an onset of glass transition at about 51° C., a half point glass transition at about 74° C., and ending of glass transition at about 117° C.

Figure 7:
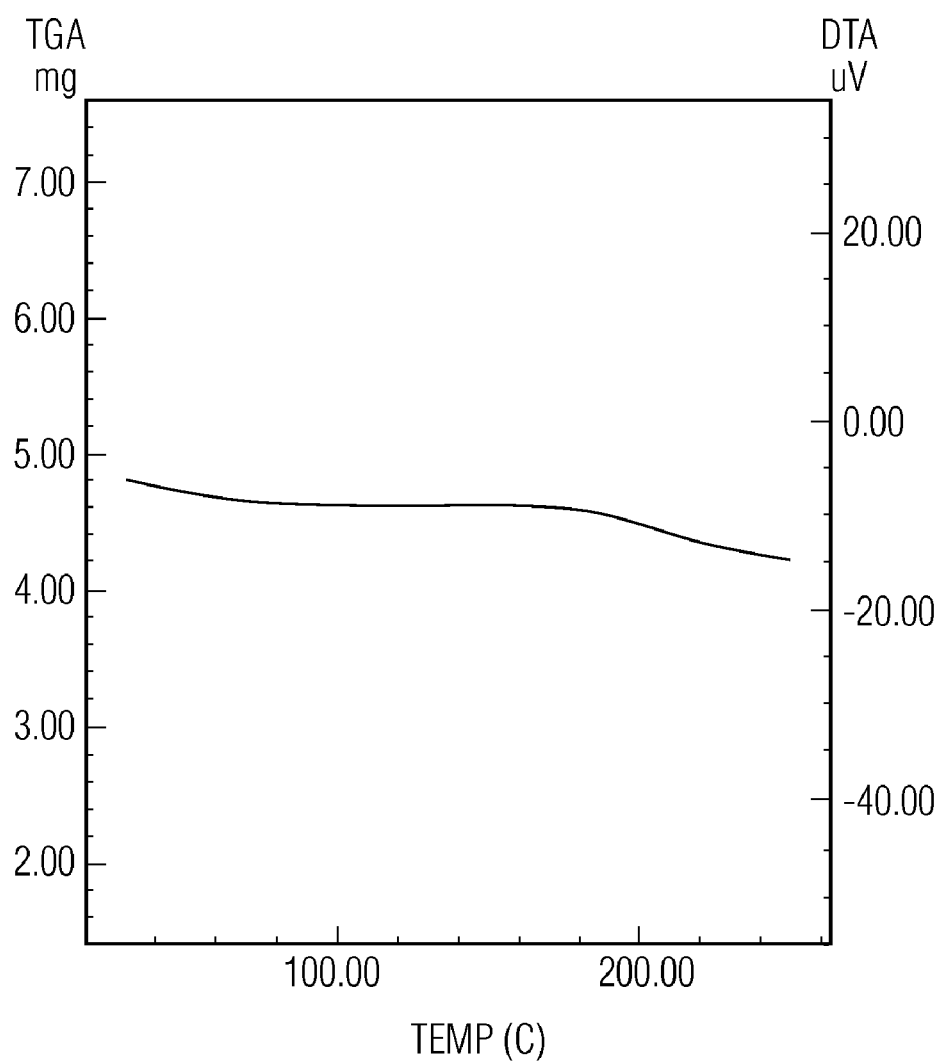
FIG. 7 is a TGA curve of the amorphous form of vardenafil monohydrochloride prepared in Example 2.

Amorphous vardenafil monohydrochloride is still further characterized by a thermogravimetric analysis curve substantially in accordance with the DTA curve of FIG. 7.

Yet more another aspect of the invention provides a process for the preparation of amorphous form of vardenafil monohydrochloride.

In an embodiment, the process for the preparation of amorphous form of vardenafil monohydrochloride comprises:

a) providing a solution of vardenafil in a suitable solvent;
b) removing the solvent; and
c) optionally, drying the solid obtained in step b).

Step a) involves providing a solution of vardenafil in a suitable solvent.

The solution of vardenafil may be obtained by dissolving vardenafil in a suitable solvent, or such a solution may be obtained directly from a reaction in which vardenafil is formed.

When the solution is prepared by dissolving vardenafil in a suitable solvent, any form of vardenafil such as the crystalline or amorphous form, including any salts, solvates and hydrates may be utilized for preparing the solution.

Suitable solvents which can be used for dissolving vardenafil include but are not limited to: alcohols such as methanol, ethanol, isopropyl alcohol, n-propanol, and the like; halogenated hydrocarbons such as dichloromethane, 1,2-dichloroethane, chloroform, carbon tetrachloride and the like; ketones such as acetone, ethyl methyl ketone, methyl isobutyl ketone and the like; esters such as ethyl acetate, n-propyl acetate, n-butyl acetate, t-butyl acetate and the like; ethers such as diethyl ether, dimethyl ether, diisopropyl ether, 1,4-dioxane and the like; hydrocarbons such as toluene, xylene, n-heptane, cyclohexane, n-hexane and the like; nitriles such as acetonitrile, propionitrile and the like; or mixtures thereof or their combinations with water in various proportions.

The dissolution temperatures can range from about 20 to 120° C. depending on the solvent used for dissolution. Any other temperature is also acceptable as long as a clear solution of vardenafil is provided.

The quantity of solvent used for dissolution depends on the solvent and the dissolution temperature adopted. The concentration of vardenafil in the solution may generally range from about 0.1 to about 10 g/ml in the solvent.

Optionally, the solution obtained above can be filtered to remove any undissolved particles.

The undissolved particles can be removed suitably by filtration, centrifugation, decantation, and other techniques. The solution can be filtered by passing through paper, glass fiber, or other membrane material, or a bed of a clarifying agent such as celite. Depending upon the equipment used and the concentration and temperature of the solution, the filtration apparatus may need to be preheated to avoid premature crystallization.

Step b) involves removing the solvent.

Removal of the solvent may be carried out suitably using evaporation, atmospheric distillation, or distillation under vacuum.

Distillation of the solvent may be conducted under a vacuum, such as below about 100 mm Hg to below about 600 mm Hg, at temperatures such as about −20° C. to about 70° C. Any temperature and vacuum conditions can be used as long as there is no increase in the impurity levels of the product.

Suitable techniques which can be used for the distillation include, distillation using a rotational evaporator device such as a Buchi Rotavapor, spray drying, freeze drying, agitated thin film drying ("ATFD"), and the like.

These techniques are applicable to both aqueous and organic solutions of vardenafil. However, solutions using the more volatile organic solvents are preferred.

Techniques such as Buchi Rotavapor drying and dry distillation under vacuum, may be suitable for laboratory-scale processes such as for quantities less than about 100 g. Other techniques such as spray drying, freeze drying and ATFD are more suitable for industrial scale production with a batch size of at least about 100 g or about 1 kg, or greater.

Step c) involves drying of the solid obtained in step b).

The amorphous material obtained from step b) can be collected from the equipment using techniques such as by scraping, or by shaking the container.

Optionally, the product obtained can be further dried. The drying can be carried out at reduced pressures, such as below about 200 mm Hg or below about 50 mm Hg, at temperatures such as about 35° C. to about 70° C. The drying can be carried out for any desired time period that achieves the desired result, such as for about 1 to 20 hours.

Still another aspect of the invention provides crystalline hydrates of vardenafil dihydrochloride characterized by their XRPD patterns, DSC curves, and TGA curves.

Crystalline hydrates of vardenafil dihydrochloride refer to the monohydrate, dihydrate, and trihydrate.

Figure 8:
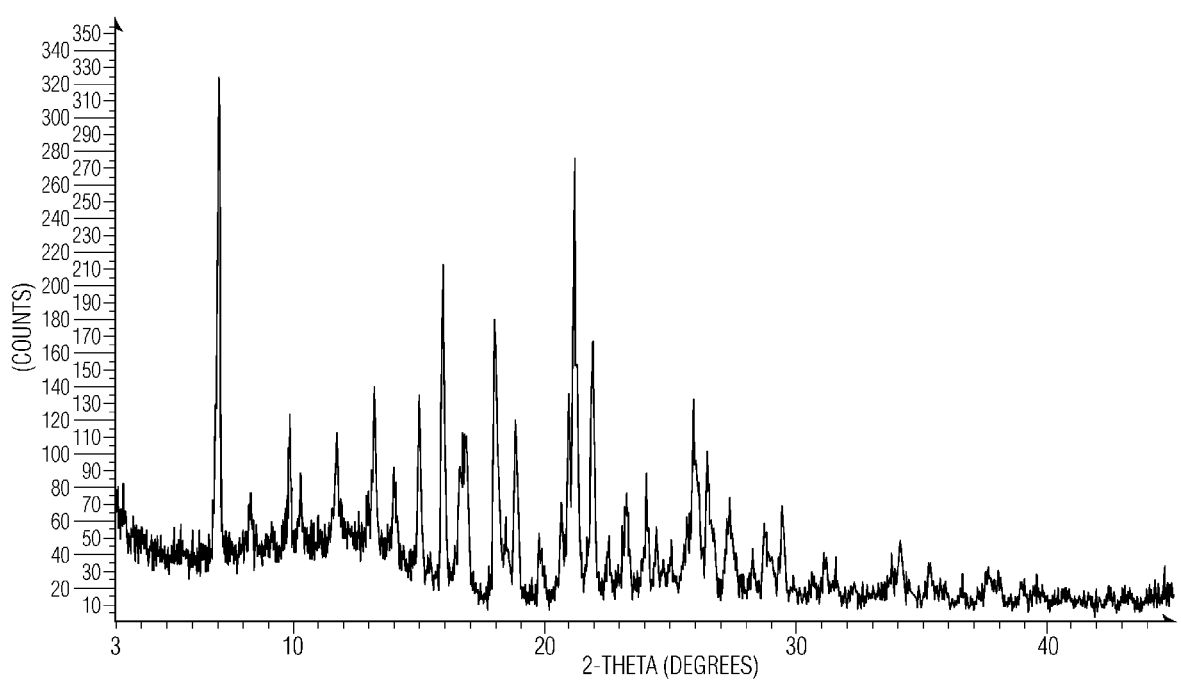
FIG. 8 is an XRPD pattern of the monohydrate of vardenafil dihydrochloride prepared in Example 4.

The crystalline monohydrate of vardenafil dihydrochloride is characterized by its XRPD pattern substantially in accordance with the pattern of FIG. 8. The crystalline monohydrate of vardenafil dihydrochloride is also characterized by an XRPD pattern having significant peaks at about 7.06, 8.3, 11.7, 21.0, 13.3, 18.1 and 21.3, 26.0, ±0.2 degrees 2θ. It is also characterized by the additional XRPD peaks at about 16.0, 26.6, and 19.0, ±0.2 degrees 2θ.

Figure 9:
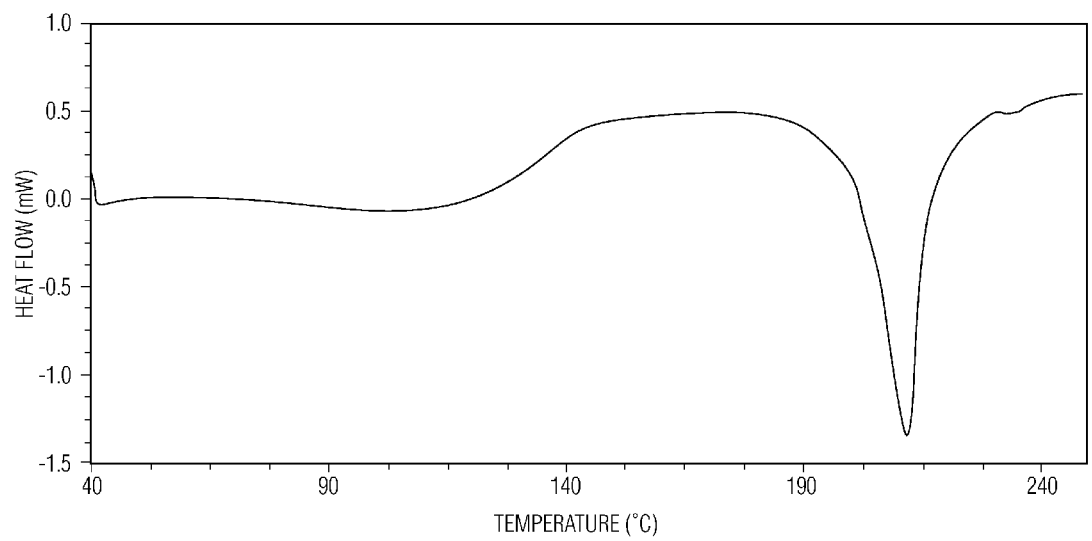
FIG. 9 is a DSC curve of the monohydrate of vardenafil dihydrochloride prepared in Example 4.

The crystalline monohydrate of vardenafil dihydrochloride is further characterized by a differential scanning calorimetry curve substantially in accordance with the curve of FIG. 9. The crystalline monohydrate of vardenafil dihydrochloride is also characterized by a DSC curve having endotherms at about 113° C. and about 211° C.

Figure 10:
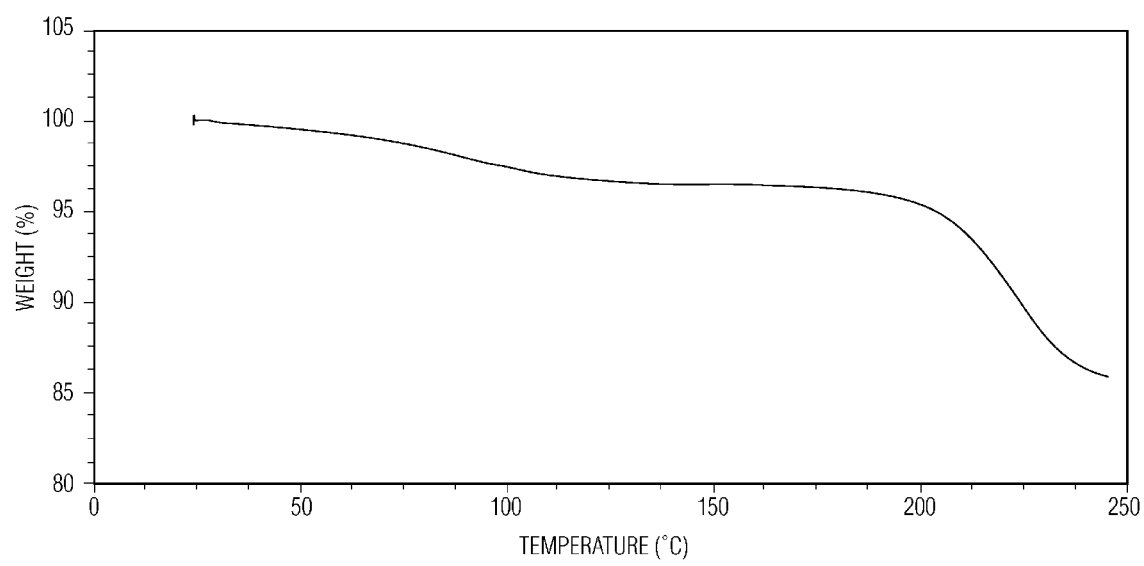
FIG. 10 is a TGA curve of the monohydrate of vardenafil dihydrochloride prepared in Example 4.

The crystalline monohydrate of vardenafil dihydrochloride is still further characterized by a thermogravimetric analysis curve substantially in accordance with the DTA curve of FIG. 10, showing a weight loss corresponding to one water molecule per mole.

Further the moisture content can be characterized using Karl Fischer reagent, and varies from about 3.5 to 4% by weight.

Figure 11:
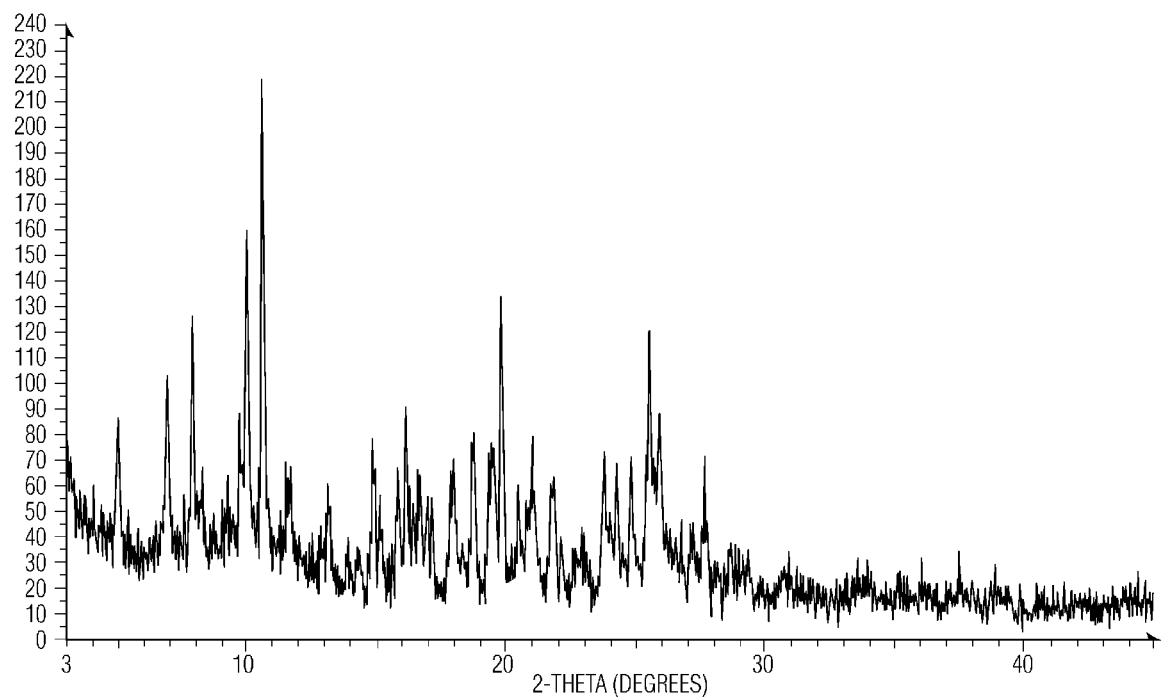
FIG. 11 is an XRPD pattern of the dihydrate of vardenafil dihydrochloride prepared in Example 5.

The crystalline dihydrate of vardenafil dihydrochloride is characterized by its XRPD pattern substantially in accordance with the pattern of FIG. 11. The crystalline dihydrate of vardenafil dihydrochloride is also characterized by an XRPD pattern having significant peaks at about 4.9, 6.9, 7.9, 10.6, 14.9, 19.5, and 9.9, ±0.2 degrees 2θ. It is also characterized by the additional XRPD peaks at about 8.16, 9.7, 11.6, and 13.1, ±0.2 degrees 2θ.

Figure 12:
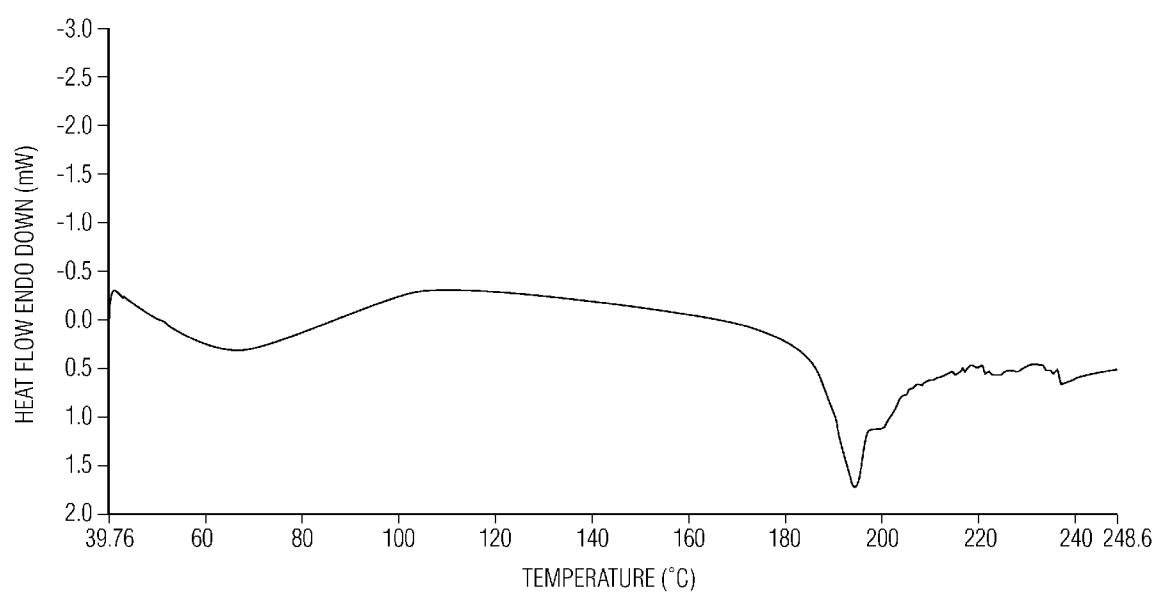
FIG. 12 is a DSC curve of the dihydrate of vardenafil dihydrochloride prepared in Example 5.

The crystalline dihydrate of vardenafil dihydrochloride is further characterized by a differential scanning calorimetry curve substantially in accordance with the curve of FIG. 12. The crystalline dihydrate of vardenafil dihydrochloride is also characterized by a DSC curve having endotherms at about 68° C. and about 194° C.

Figure 13:
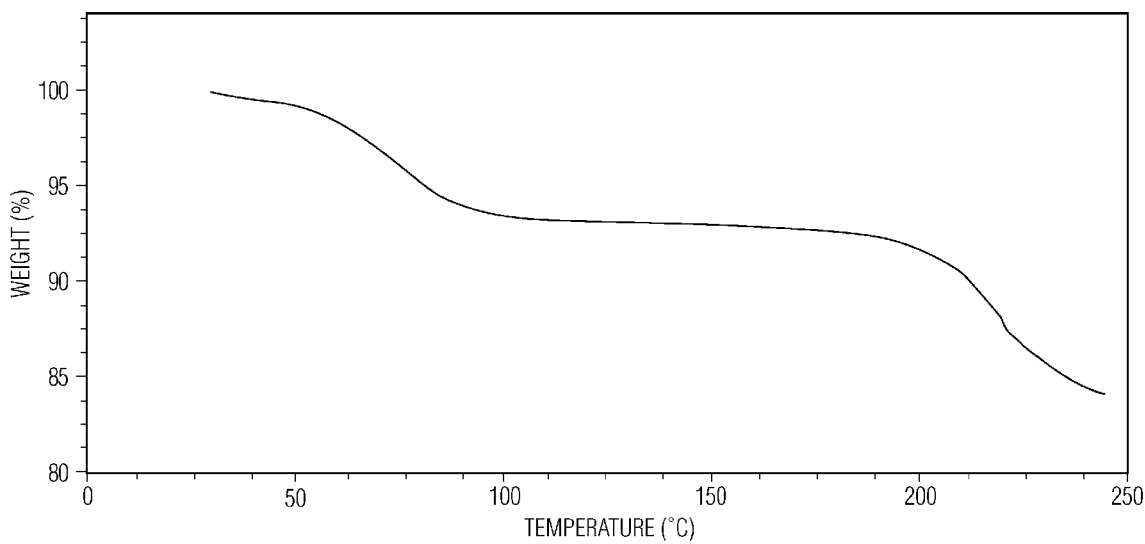
FIG. 13 is a TGA curve of the dihydrate of vardenafil dihydrochloride prepared in Example 5.

The crystalline dihydrate of vardenafil dihydrochloride is still further characterized by a thermogravimetric analysis curve substantially in accordance with the DTA curve of FIG. 13, showing a weight loss corresponding to two water molecules per mole.

Further the moisture content can be characterized using Karl Fischer reagent, and varies from about 6 to 6.5% by weight.

Figure 14:
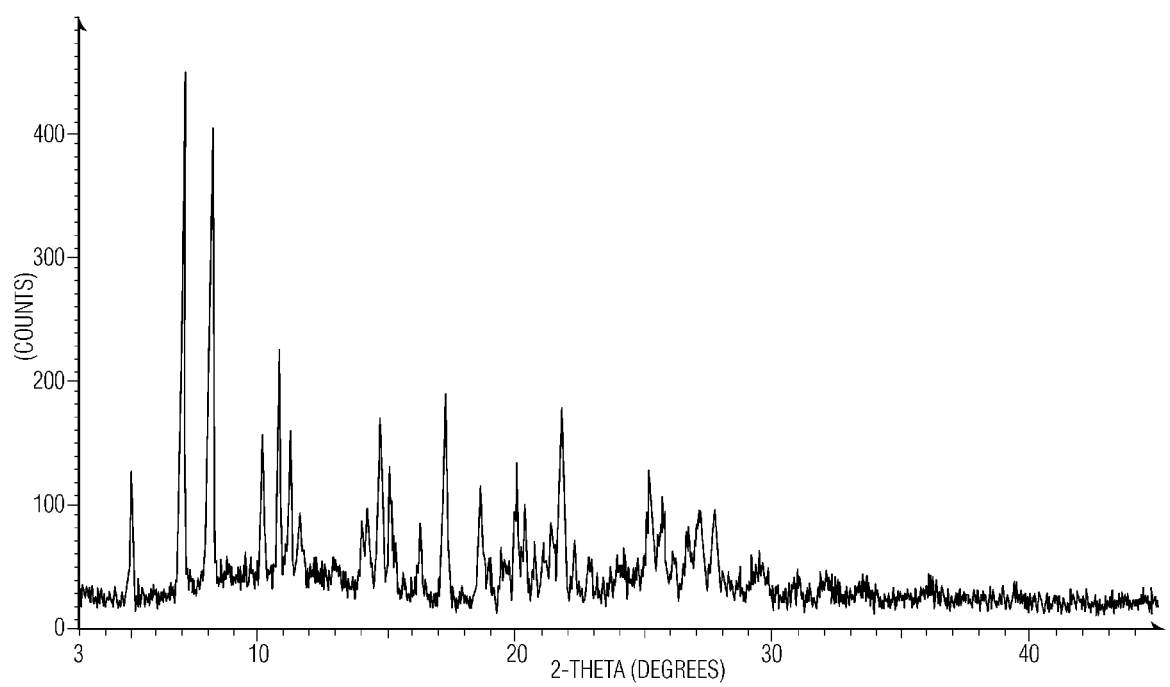
FIG. 14 is an XRPD pattern of the trihydrate of vardenafil dihydrochloride prepared in Example 6.

The crystalline trihydrate of vardenafil dihydrochloride is characterized by its XRPD pattern substantially in accordance with the pattern of FIG. 14. The crystalline trihydrate of vardenafil dihydrochloride is also characterized by an XRPD pattern having significant peaks at about 7.0, 10.7, 11.1, 14.2, 14.8, 17.2, 21.7, 25.2, 26.7, and 5.0, ±0.2 degrees 2θ. It is also characterized by the additional XRPD peaks at about 10.0, 15.0, 18.6, and 25.2, ±0.2 degrees 2θ.

Figure 15:
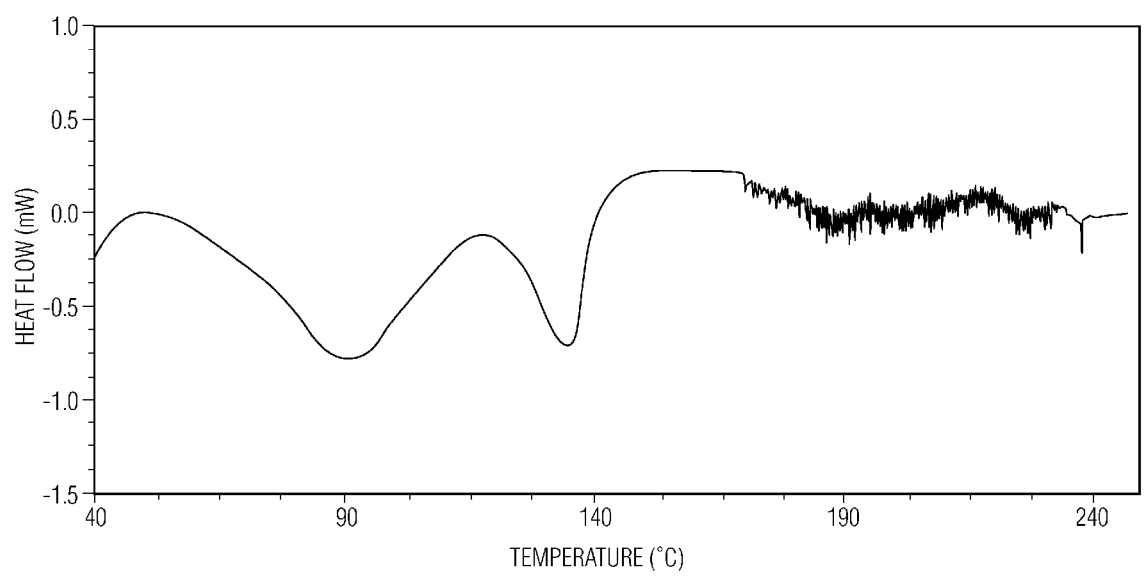
FIG. 15 is a DSC curve of the trihydrate of vardenafil dihydrochloride prepared in Example 6.

The crystalline trihydrate of vardenafil dihydrochloride is further characterized by a differential scanning calorimetry curve substantially in accordance with the curve of FIG. 15. The crystalline dihydrate of vardenafil dihydrochloride is also characterized by a DSC curve having endotherms at about 90° C. and about 135° C.

Figure 16:
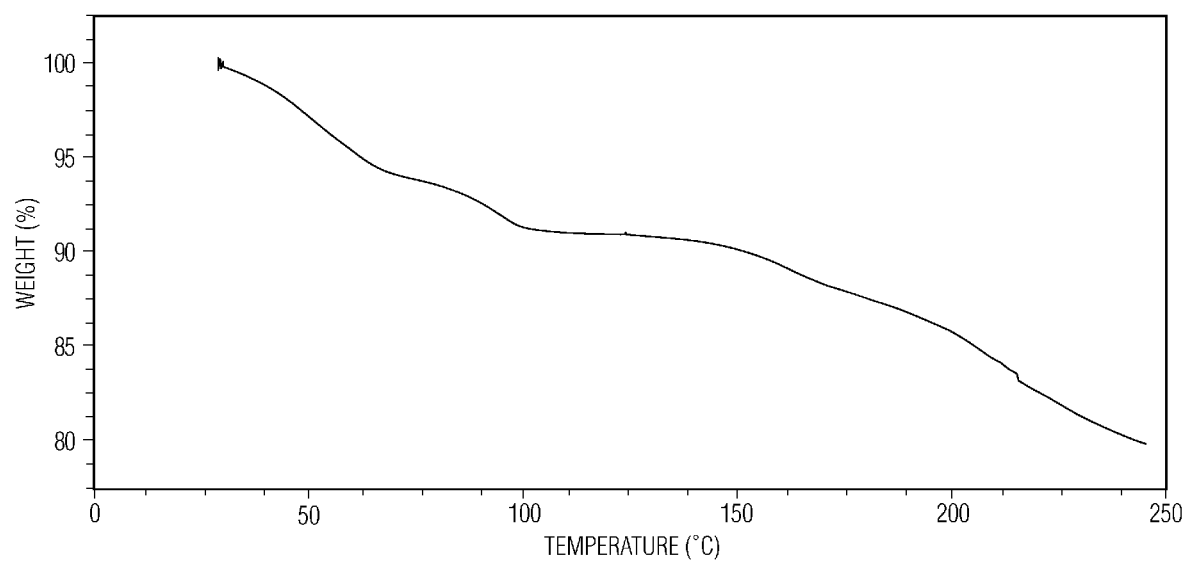
FIG. 16 is a TGA curve of the trihydrate of vardenafil dihydrochloride prepared in Example 6.

The crystalline trihydrate of vardenafil dihydrochloride is still further characterized by a thermogravimetric analysis curve substantially in accordance with the DTA curve of FIG. 16.

Still another aspect of the invention provides processes for the preparation of crystalline hydrates of vardenafil hydrochloride.

In an embodiment, the process for preparation of crystalline hydrates of vardenafil hydrochloride comprises:

a) providing a solution of vardenafil in a suitable solvent;
b) adding hydrochloric acid;
c) crystallizing the solid from the solution; and
d) drying the solid.

Step a) involves providing a solution of vardenafil in a suitable solvent;

The solution of vardenafil may be obtained by dissolving vardenafil in a suitable solvent, or such a solution may be obtained directly from a reaction in which vardenafil is formed.

When the solution is prepared by dissolving vardenafil in a suitable solvent, any form of vardenafil such as the crystalline or amorphous form, including any salts, solvates and hydrates may be utilized for preparing the solution.

Suitable solvents which can be used for dissolving vardenafil include but are not limited to alcohols such as methanol, ethanol, isopropyl alcohol, n-propanol, and the like; ketones such as acetone, ethyl methyl ketone, methyl isobutyl ketone and the like; ethers such as diethyl ether, dimethyl ether, diisopropyl ether, 1,4-dioxane and the like in combinations with water in various proportions.

The ratio of the organic solvent to water can range from about 12:1 to about 14:1 w/w. And the quantity of the aqueous solvent used to dissolve vardenafil can range from about 2 times to the weight of vardenafil to about 3.5 times to the weight of vardenafil.

The dissolution temperatures can range from about 20 to 120° C. depending on the solvent used for dissolution. Any other temperature is also acceptable as long as a clear solution of vardenafil is provided.

The quantity of solvent used for dissolution depends on the solvent and the dissolution temperature adopted. The concentration of vardenafil in the solution may generally range from about 0.1 to about 10 g/ml in the solvent.

Optionally, the solution obtained above can be filtered to remove any undissolved particles before further processing.

The undissolved particles can be removed suitably by filtration, centrifugation, decantation, and other techniques. The solution can be filtered by passing through paper, glass fiber, or other membrane material, or a bed of a clarifying agent such as celite. Depending upon the equipment used and the concentration and temperature of the solution, the filtration apparatus may need to be preheated to avoid premature crystallization.

Step b) involves adding hydrochloric acid;

Hydrochloric acid is added to the solution obtained in step a) to form the vardenafil hydrochloride salt. To form a dihydrochloride salt, vardenafil and hydrochloric acid are taken in a mole ratio of about 1:2. The hydrochloric acid used may be aqueous or it can be dissolved in any of the solvents listed for the purpose of dissolution.

Step c) involves crystallizing the solid from the solution;

For crystallization to occur, the reaction mass may be maintained further at temperatures lower than the solution formation or concentration temperatures such as for example below about 10° C. to about 25° C., for a period of time as required for a more complete isolation of the product. The exact cooling temperature and time required for complete isolation can be readily determined by a person skilled in the art and will also depend on parameters such as concentration and temperature of the solution or slurry.

Optionally isolation may be enhanced by methods such as cooling, partial removal of the solvent from the mixture, by adding an anti-solvent to the reaction mixture or a combination thereof.

Optionally, small amounts of seeding crystals of the desired hydrate of the vardenafil hydrochloride salt may be added to the reaction mixture. Suitably, small amounts are about 1 to 20 weight %, more preferably about 5 weight %. Seeding crystals may be added before or, where appropriate, after the step initiating the precipitation.

The method by which the solid material is recovered from the final mixture, with or without cooling below the operating temperature, can be any of techniques such as filtration by gravity, or by suction, centrifugation, and the like. The crystals so isolated can carry a small proportion of occluded mother liquor containing a higher percentage of impurities. If desired the crystals can be washed on the filter with a solvent to wash out the mother liquor.

Step d) involves drying of the solid.

The selection of the drying conditions for obtained wet solid is important, as the drying conditions contribute to the nature of the hydrate obtained.

Drying of the wet compound over a period of 1½ to 2½ hours at a temperature of about 43 to 45° C., leads to the formation of crystals of the monohydrate of vardenafil dihydrochloride.

Drying of the wet compound over a period of 1 to 2 hours at a temperature of about 39 to 42° C., leads to the formation of crystals of the dihydrate of vardenafil dihydrochloride.

Drying of the wet compound over a period of 1 to 1½ hours at a temperature of about 40 to 45° C., leads to the formation of the trihydrate of vardenafil dihydrochloride.

A still further aspect of the invention provides a pharmaceutical composition comprising vardenafil or its pharmaceutically acceptable salts prepared in accordance with this invention along with one or more pharmaceutically acceptable carriers, excipients or diluents.

The pharmaceutical composition comprising vardenafil or its pharmaceutically acceptable salts of the invention along with one or more pharmaceutically acceptable carriers may further formulated as: solid oral dosage forms such as, but not limited to, powders, granules, pellets, tablets, and capsules; liquid oral dosage forms such as but not limited to syrups, suspensions, dispersions, and emulsions; and injectable preparations such as but not limited to solutions, dispersions, and freeze dried compositions. Formulations may be in the form of immediate release, delayed release or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared by direct blending, dry granulation or wet granulation or by extrusion and spheronization. Compositions may be presented as uncoated, film coated, sugar coated, powder coated, enteric coated or modified release coated. Compositions of the present invention may further comprise one or more pharmaceutically acceptable excipients.

Pharmaceutically acceptable excipients that find use in the present invention include, but are not limited to: diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, polyvinyl pyrrolidone, hydroxypropyl cellulose, hydroxypropyl methylcellulose, pregelatinized starch and the like; disintegrants such as starch, sodium starch glycolate, pregelatinized starch, crospovidone, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants; complex forming agents such as various grades of cyclodextrins, resins; release rate controlling agents such as hydroxypropyl cellulose, hydroxymethyl cellulose, hydroxypropyl methylcellulose, ethyl cellulose, methyl cellulose, various grades of methyl methacrylates, waxes and the like. Other pharmaceutically acceptable excipients that are of use include but are not limited to film formers, plasticizers, colorants, flavoring agents, sweeteners, viscosity enhancers, preservatives, antioxidants and the like.

In the compositions of the present invention vardenafil or its pharmaceutically acceptable salts is a useful active ingredient when present in the range of 0.5 mg to 50 mg, or 1 mg to 25 mg.

Certain specific aspects and embodiments of this invention are described in further detail by the examples below, which examples are not intended to limit the scope of the appended claims in any manner. In the examples, moisture content was determined by the Karl Fischer method.

EXAMPLE 1

Preparation of Crystalline form II of Vardenafil Free Base 14.0 g of vardenafil was charged into a four neck round bottom flask containing 70 ml of isopropyl alcohol and heated to about 82° C. An additional 70 ml of isopropyl alcohol was added slowly to get complete dissolution. The undissolved solid particles were filtered through a perlite bed to get a particle free solution. The filtrate was charged into a clean round bottom flask and was allowed to cool to 20° C. for crystallization. The solid was filtered and washed with 10 ml of isopropyl alcohol. The material was dried at 44° C. under vacuum for 2 hours to give 12.6 g (90% yield) of crystalline Form II of vardenafil free base.

EXAMPLE 2

Preparation of Amorphous Vardenafil Hydrochloride 2.0 g of vardenafil hydrochloride and 80 ml of water was charged into a round bottom flask and stirred for about 45 minutes at ambient temperature for clear dissolution. The undissolved material was filtered and the resultant solution was cooled to −5° C. The final product was freeze dried at −5° C. to remove the water to afford 1.8 g of the desired amorphous form of vardenafil hydrochloride.

Moisture content by Karl Fischer: 4.5% w/w.

EXAMPLE 3

Preparation of the Crystalline form II of Vardenafil Free Base 28 ml of chlorosulphonic acid was charged into a round bottom flask and cooled to about 0-5° C. 14 g of 2-(2-ethoxyphenyl)-5-methyl-7-propyl-3H-imidazo[5,1-f][1,2,4]-triazin-4-one was added to it at about 2° C. The temperature was raised to about 22° C. and maintained for about 45 minutes. The reaction mixture was slowly quenched into ice. 350 ml of dichloromethane was added and stirred for 25 minutes and then 150 ml of water was added and stirred for 10 minutes and the organic and aqueous layers were separated. The organic layer was charged into a round bottom flask and cooled to −3° C. 10.4 ml of N-ethylpiperazine diluted with 15 ml of dichloromethane was added at about −3° C. The temperature was raised to about 25° C. and maintained for 45 minutes. The reaction mixture was washed with 140 ml of water in two equal lots. The organic layer was completely distilled off at 41° C. and a vacuum of 300 mm Hg and then 98 ml of 4% aqueous acetone was added to it. The suspension was heated to 55° C. for dissolution. The solution was then cooled to about 2° C. and maintained for about 60 minutes for crystallization. The solid was filtered under vacuum and washed with 14 ml of pre-cooled 4% aqueous acetone solution. The solid was dried at 48° C. for about 3 hours to afford 11.8 g of the desired crystalline Form II of vardenafil free base.

EXAMPLE 4

Preparation of the Monohydrate of Vardenafil Dihydrochloride 10 g of vardenafil free base was taken into a round bottom flask and a mixture of 24 ml of acetone and 2 ml of water (a ratio of 12:1 v/v) was added and stirred for about 10 minutes at 28° C. 3 ml of 36% conc. aqueous hydrochloric acid was added with stirring to the reaction mixture and heated to a temperature of 55° C. for 30 minutes. The reaction mixture was cooled to a temperature of 20° C. and then further cooled to a temperature of about 5° C. The reaction mixture was then seeded with vardenafil dihydrochloride dihydrate at 3° C. The solid was filtered and washed with 15 ml of acetone and subjected to suction drying. The solid mass was transferred into an oven and dried at a temperature of 44° C. for 2 hours to yield 8.4 g of the monohydrate of vardenafil dihydrochloride.

Moisture content: 3.6% by weight.
Melting point range: 233° C. to 238° C.

EXAMPLE 5

Preparation of the Dihydrate of Vardenafil Dihydrochloride 11 g of vardenafil free base was taken into a round bottom flask followed by the addition of 39 ml of a mixture of acetone and water in the ratio of 12:1 v/v at 29° C. 3 ml of 36% concentrated hydrochloric acid was added to the above reaction mass and heated to a temperature of 55° C. and maintained for 30 minutes. It was then cooled to temperature of about 45° C. followed by distillation under vacuum of 280 torr and 45° C. The resultant reaction mass was cooled to 20° C. followed by the addition of 50 ml of diethyl ether with simultaneous stirring and the reaction mass was filtered at 20° C. The solid material was washed with 20 ml of ether and the material was dried at 40° C. for 1.5 hours to yield 10.5 g of the dihydrate of vardenafil dihydrochloride.

Moisture content: 6% by weight.
Melting point range: 214° C. to 232° C.

EXAMPLE 6

Preparation of the Trihydrate of Vardenafil Dihydrochloride 24 g of vardenafil free base was taken into a round bottom flask followed by the addition of 60 ml of a mixture of acetone and water in the ratio of 12:1 v/v at 28° C. 7.2 ml of 36% aqueous hydrochloric acid was added to the above reaction mass and heated to 56° C., and maintained for 30 minutes. It was then cooled to temperature of 5° C. and the reaction mass was then seeded with vardenafil dihydrochloride dihydrate at 3° C. to get a solid. The reaction material was filtered by applying vacuum of about 280 torr, washed with 35 ml of acetone and subjected to suction drying. The solid mass was transferred into a oven and dried at a temperature of 45° C. for 1.5 hours to yield 23.6 g of the trihydrate of vardenafil dihydrochloride.

Moisture content: 12.1% by weight.
Melting point range: 224° C. to 239° C.

EXAMPLE 7

Preparation of the Trihydrate of Vardenafil Monohydrochloride 14 g of vardenafil hydrochloride was taken into a round bottom flask followed by the addition of 70 ml water and the pH of the reaction mass was adjusted using sodium hydroxide to 11 at 30° C. 280 ml of dichloromethane was added to the above reaction mass and the layers were separated. The organic layer was dried over sodium sulfate and the organic layer was transferred into a round bottom flask and subjected to heating for distillation at 40° C. for 1.5 hours. The solid material was transferred into a round bottom flask and 36 ml of a mixture of acetone and water in 12:1 ratio was added with stirring, then 2.2 ml of 36% aqueous hydrochloric acid was added with stirring. The reaction mass was heated to a temperature of about 45° C. and the undissolved particles were removed by filtration. The filtrate was taken into a round bottom flask and cooled to 5° C., maintained for 45 minutes at 3 to 5° C. followed by the filtration of the solid which was then subjected to suction drying and finally dried at 40° C. to yield 9.0 g of the trihydrate of vardenafil monohydrochloride.

We claim:
1. Crystalline Form II of vardenafil.
2. A process for preparing crystalline Form II of vardenafil of claim 1, comprising crystallizing vardenafil from isopropanol.
3. Amorphous vardenafil hydrochloride.
4. A process for preparing amorphous vardenafil hydrochloride of claim 3, comprising freeze drying an aqueous solution of vardenafil hydrochloride.
5. Crystalline Form II of vardenafil of claim 1, having an X-ray diffraction pattern with copper K α radiation, having significant peaks at about 16.4, 11.2, 15.8, 13.8, 7.8, 9.1, 17.3, 17.6, 18.3, 23.7, 24.2, 24.3, 24.6, 25.5, and 12.3±0.2 degrees 2θ.
6. Amorphous vardenafil monohydrochloride of claim 3 characterized by a DSC curve having an onset of glass transition at about 51° C., a half point glass transition at about 74° C., and ending of glass transition at about 117° C.

* * * * *